(12) United States Patent
Mattke et al.

(10) Patent No.: US 8,487,127 B2
(45) Date of Patent: Jul. 16, 2013

(54) PROCESS FOR PREPARING ISOCYANATES IN THE GAS PHASE

(75) Inventors: Torsten Mattke, Freinsheim (DE); Ralf Boehling, Lorsch (DE); Carsten Knoesche, Niederkirchen (DE); Vanessa Simone Lehr, Mannheim (DE)

(73) Assignee: BASF SE, Ludwigshafen (DE)

( * ) Notice: Subject to any disclaimer, the term of this patent is extended or adjusted under 35 U.S.C. 154(b) by 328 days.

(21) Appl. No.: 13/035,166

(22) Filed: Feb. 25, 2011

(65) Prior Publication Data

US 2011/0213177 A1    Sep. 1, 2011

Related U.S. Application Data

(60) Provisional application No. 61/308,318, filed on Feb. 26, 2010.

(51) Int. Cl.
*C07C 263/10* (2006.01)
(52) U.S. Cl.
USPC .......................................... 560/338; 560/347
(58) Field of Classification Search
USPC .................................. 560/347, 338
See application file for complete search history.

(56) References Cited

U.S. PATENT DOCUMENTS

| | | | |
|---|---|---|---|
| 2005/0022940 A1* | 2/2005 | Kupper et al. | 159/47.1 |
| 2007/0043233 A1* | 2/2007 | Sanders et al. | 560/347 |

FOREIGN PATENT DOCUMENTS

| | | |
|---|---|---|
| EP | 1 319 655 A2 | 6/2003 |
| EP | 1 555 258 A1 | 7/2005 |
| EP | 1 754 698 A2 | 2/2007 |

OTHER PUBLICATIONS

U.S. Appl. No. 13/587,378, filed Aug. 16, 2012, Mattke, et al.
U.S. Appl. No. 13/661,652, filed Oct. 26, 2012, Leschinski, et al.
U.S. Appl. No. 13/687,670, filed Nov. 28, 2012, Mattke, et al.
U.S. Appl. No. 13/434,135, filed Mar. 29, 2012, Lehr, et al.

* cited by examiner

*Primary Examiner* — Johann R Richter
*Assistant Examiner* — Pancham Bakshi
(74) *Attorney, Agent, or Firm* — Oblon, Spivak, McClelland, Maier & Neustadt, L.L.P.

(57) ABSTRACT

The invention relates to a process for preparing isocyanates by reacting the corresponding amines with phosgene in the gas phase, in the presence or absence of an inert medium, which comprises the following steps:
(a) vaporization of the amine in a vaporizer,
(b) superheating of the amine,
(c) mixing of the gaseous amine with the phosgene and introduction into a reaction zone,
(d) reaction of amine and phosgene to give isocyanate in the reaction zone, with a reaction mixture comprising isocyanate and hydrogen chloride being formed,
(e) cooling of the reaction mixture comprising isocyanate and hydrogen chloride,
wherein the vaporizer comprises a vessel in which tubes through which a heating medium flows are comprised, where number and diameter of the tubes are designed so that the tubes have a specific heat transfer area based on the volume through which the amine flows of at least 300 $m^2/m^3$.

12 Claims, No Drawings

PROCESS FOR PREPARING ISOCYANATES IN THE GAS PHASE

The invention relates to a process for preparing isocyanates by reacting the corresponding amines with phosgene in the gas phase, in the presence or absence of an inert medium, which comprises the following steps:

(a) vaporization of the amine in a vaporizer,
(b) superheating of the amine,
(c) mixing of the gaseous amine with the phosgene and introduction into a reaction zone,
(d) reaction of amine and phosgene to give isocyanate in the reaction zone, with a reaction mixture comprising isocyanate and hydrogen chloride being formed,
(e) cooling of the reaction mixture comprising isocyanate and hydrogen chloride.

The preparation of isocyanates by phosgenation of the corresponding amines can in principle be carried out by means of a liquid-phase phosgenation or a gas-phase phosgenation. The gas-phase phosgenation makes a higher selectivity possible and requires a lower hold-up of toxic phosgene and a reduced energy input.

In the gas-phase phosgenation, an amine-comprising feed stream and a phosgene-comprising feed stream are mixed in the gaseous state. The amine and the phosgene react to form the corresponding isocyanates with liberation of hydrogen chloride (HCl). The amine-comprising feed stream is generally present in a liquid phase and has to be vaporized and optionally superheated before mixing with the phosgene-comprising stream.

Corresponding processes for preparing isocyanates in the gas phase are described, for example, in EP-A 1 319 655 or EP-A 1 555 258.

To avoid subsequent reactions, the reaction mixture is quickly cooled after the reaction is complete. This is carried out using, for example, a liquid quench.

To vaporize the amine and superheat it to a reaction temperature of above 300° C., essentially electric heating, combustion gases or steam under high pressure are used at present. If appropriate, a salt melt is also used as heat transfer medium. During the vaporization and superheating of the amine at high temperatures, decomposition and oligomerization reactions can occur. This leads firstly to a decrease in yield of the overall process, and secondly higher oligomers formed can remain unvaporized and lead to deposits in the vaporizer and in plant components following the vaporizer. To minimize yield losses and the risk of blockages, it is necessary to adhere to short vaporization and superheating times for the amine. These are achieved essentially by high volume-based heat transfer areas. For the present purposes, the volume-based heat transfer area is the ratio of heat-transferring surface to the volume through which the amine to be vaporized flows. A vaporizer in which the amine is conveyed through channels and which provides a specific heat transfer area of 1000 $m^2/m^3$ is known from EP-A 1 754 698. However, the vaporizer described has the disadvantage that there is physical separation of the flow paths in the individual channels. If deposits are formed in a channel, less flows through this and as a result the residence times in the channel increase, leading to increased decomposition of the amine with further formation of deposits. This leads to blockage of the channel. The heat transfer area of this channel is therefore no longer available for vaporization. At a constant volume flow, greater flow at the same time occurs through the other, remaining channels, resulting in increased pressure drops and shorter residence times, which may lead to the amine not being completely vaporized. The use of parallel channel structures through which the amine flows is therefore very sensitive to deposits in individual channels. A further problem which occurs when the amine flows through individual channels is uniform distribution of the amine over all channels.

It is therefore an object of the present invention to provide a process for preparing isocyanates by reacting the corresponding amines with phosgene in the gas phase, in which the amine is vaporized in a vaporizer having a high specific heat transfer area and thus short vaporization and superheating times, which process does not have the disadvantages of vaporizers known from the prior art.

The object is achieved by a process for preparing isocyanates by reacting the corresponding amines with phosgene in the gas phase, in the presence or absence of an inert medium, which comprises the following steps:

(a) vaporization of the amine in a vaporizer,
(b) superheating of the amine,
(c) mixing of the gaseous amine with the phosgene and introduction into a reaction zone,
(d) reaction of amine and phosgene to give isocyanate in the reaction zone, with a reaction mixture comprising isocyanate and hydrogen chloride being formed,
(e) cooling of the reaction mixture comprising isocyanate and hydrogen chloride, wherein the vaporizer comprises a vessel in which tubes through which a heating medium flows are comprised, where number and diameter of the tubes are designed so that the tubes have a specific heat transfer area based on the volume through which the amine flows of at least 300 $m^2/m^3$.

For the purposes of the present invention, the specific heat transfer area is the surface around which the amine flows of all tubes which are comprised in the vaporizer and through which heating medium flows based on the volume through which the amine flows.

The advantage of the heating medium flowing through the tubes of the vaporizer and the amine flowing around the tubes is that the flow paths of the amine do not have to be divided over individual channels. In addition, the comparatively large contiguous area through which the amine flows avoids possible formation of deposits which accelerate the decomposition of the amine and thus the formation of further deposits. The formation of a low level of deposits leads only to a minimal increase in the pressure drop and thus also to a firstly insignificant shortening of the residence time. The vaporizer can thus initially still be used without restrictions in the event of deposits being formed. In addition, the unchanged high flow velocity of the amine leads, even when a low level of deposits is formed, to the deposits being at least partly entrained in the amine stream and the risk of formation of deposits thus being reduced further.

To achieve rapid vaporization and if appropriate superheating of the amine, a large specific heat transfer area is selected. According to the invention, the heat transfer area is at least 300 $m^2/m^3$. The specific heat transfer area based on the volume through which the amine flows is preferably at least 400 $m^2/m^3$ and in particular at least 500 $m^2/m^3$.

To achieve rapid vaporization of the amine and also to avoid the formation of deposits on the heat transfer surfaces, preference is also given to the tubes being arranged parallel to the flow direction of the amine in the vessel. Here, the heating medium can flow through the tubes either in cocurrent with the amine or in countercurrent to the amine. Preference is given to the heating medium flowing in countercurrent through the tubes.

To reduce the formation of deposits on the surfaces of the tubes further, preference is given, in an embodiment of the invention, to the tubes having a smooth surface. Here, a smooth surface is, in particular, a surface without ribs or other protuberances and without grooves. Furthermore, a low roughness of the surface of the tubes is also advantageous. The lower the roughness of the surface, the fewer nuclei to which deposits can become attached are present on the surface.

To achieve a uniform flow of the amine around the tubes, preference is also given to the tubes having a circular cross section. However, any cross section other than a circular cross section is also possible. An advantage of a circular cross section is that the tubes have no edges at which deposits can be formed. In addition, tubes having a circular cross section make it possible to use a large number of tubes and thus a large specific heat transfer area.

To obtain the specific heat transfer area based on the volume through which the amine flows of at least 300 $m^2/m^3$, tubes having an external diameter of not more than 10 mm, preferably not more than 8 mm, are preferably used in the vaporizer. The smallest distance between two adjacent tubes is preferably not more than 3 mm. The tube diameter of not more than 10 mm and the spacing between two tubes of not more than 3 mm leads to a high specific heat transfer area based on the volume through which the amine flows.

The residence time necessary for vaporization and if appropriate superheating of the amine is set via the corresponding length of the vaporizer and thus of the tubes and also the volume flow passing through the vaporizer. The higher the volume flow at a constant area through which the amine flows, the higher the velocity and thus the shorter the residence time of the amine in the vaporizer. To increase the residence time at a given cross-sectional area through which the amine flows and a given volume flow, it is necessary to make the tubes and thus the vaporizer longer. In a vaporizer used for vaporizing and if appropriate superheating amine, the length of the tubes is preferably in the range from 0.1 to 5 m, more preferably in the range from 0.2 to 3 m and in particular in the range from 0.3 to 2 m.

Apart from vaporizing the amine in the vaporizer, it is also possible to feed the amine into the vaporizer at a temperature below the vaporization temperature and firstly preheat it to a vaporization temperature in the vaporizer. After the vaporization temperature has been reached, the amine is vaporized in the vaporizer. Since the reaction temperature for reaction of the amine with phosgene to form the corresponding isocyanate is above the vaporization temperature of the amine, usually in the range from 300 to 400° C., it is necessary to superheat the amine after vaporization. The superheating of the amine is preferably likewise carried out in the vaporizer.

The pressure at which the amine is vaporized in the vaporizer is preferably in the range from 0.05 to 10 bar abs. The pressure is particularly preferably in the range from 0.8 to 5 bar abs.

After superheating, the amine is mixed with the phosgene. Here, the temperature of the phosgene is preferably in the range from 250 to 450° C. Heating of the phosgene can be effected in any desired way known to those skilled in the art. For example, it is possible to use a heat exchanger which has the same structure as the heat exchanger in which the amine is vaporized and superheated for heating the phosgene. However, any other heat exchanger can also be used for heating the phosgene. This is possible, in particular, because the phosgene does not decompose to form deposits at the temperatures to which it is heated. It is therefore not necessary to heat the phosgene particularly quickly.

After mixing, the phosgene and the amine are fed to a reaction zone. Mixing is usually carried out in a mixing zone. The mixing zone and the reaction zone can be successive parts of a reactor as is used for preparing isocyanates by gas-phase phosgenation of amines. In general, a tube reactor is used as reactor. In the reactor, the amine is reacted with the phosgene to form the corresponding isocyanate and hydrogen chloride. The phosgene is usually introduced in excess, so that the reaction gas leaving the reactor comprises not only the isocyanate formed and the hydrogen chloride but also phosgene.

Amines which can be used for preparing isocyanates are monoamines, diamines, triamines or higher-valent amines. Preference is given to using monoamines or diamines. Corresponding to the amine used, the corresponding monoisocyanates, diisocyanates, triisocyanates or higher-valent isocyanates are obtained. The process of the invention is preferably used for preparing monoisocyanates or diisocyanates.

Diamines and diisocyanates can be aliphatic, cycloaliphatic or aromatic.

Cycloaliphatic isocyanates are isocyanates which comprise at least one cycloaliphatic ring system.

Aliphatic isocyanates are isocyanates which have exclusively isocyanate groups bound to straight or branched chains.

Aromatic isocyanates are isocyanates which have at least one isocyanate group bound to at least one aromatic ring system.

The designation "(cyclo)aliphatic isocyanates" will hereinafter be used for cycloaliphatic and/or aliphatic isocyanates.

Examples of aromatic monoisocyanates and diisocyanates are preferably ones having from 6 to 20 carbon atoms, for example phenyl isocyanate, monomeric 2,4'- and/or 4,4'-methylenedi(phenyl isocyanate) (MDI), 2,4- and/or 2,6-tolylene diisocyanate (TDI) and 1,5- or 1,8-naphthyl diisocyanate (NDI).

Examples of (cyclo)aliphatic diisocyanates are aliphatic diisocyanates such as tetramethylene 1,4-diisocyanate, hexamethylene 1,6-diisocyanate (1,6-diisocyanato-hexane), 1,8-octamethylene diisocyanate, 1,10-decamethylene diisocyanate, 1,12-dodecamethylene diisocyanate, 1,14-tetradecamethylene diisocyanate, 1,5-diisocyanatopentane, neopentane diisocyanate, derivatives of lysine diisocyanate, tetramethylxylylene diisocyanate (TMXDI), trimethylhexane diisocyanate or tetramethylhexane diisocyanate, and also 3(or 4),8(or 9)-bis(isocyanatomethyl)tricyclo-[5.2.1.0$^{2.6}$]decane isomer mixtures, and also cycloaliphatic diisocyanates such as 1,4-, 1,3- or 1,2-diisocyanatocyclohexane, 4,4'- or 2,4'-di(isocyanatocyclohexyl)methane, 1-isocyanato-3,3,5-trimethyl-5-(isocyanatomethyl)cyclohexane (isophorone diisocyanate), 1,3- or 1,4-bis(isocyanatomethyl)cyclohexane, 2,4- or 2,6-diisocyanato-1-methylcyclohexane.

Preferred (cyclo)aliphatic diisocyanates are 1,6-diisocyanatohexane, 1-isocyanato-3,3,5-trimethyl-5-(isocyanatomethyl)cyclohexane, 4,4'-di(isocyanatocyclohexyl)-methane and tolylene diisocyanate isomeric mixtures. Particular preference is given to 1,6-diisocyanatohexane, 1-isocyanato-3,3,5-trimethyl-5-(isocyanatomethyl)cyclohexane and 4,4'-di(isocyanatocyclohexyl)methane.

Amines used in the process of the invention for the reaction to form the corresponding isocyanates are ones for which the amine, the corresponding intermediates and the corresponding isocyanates are present in gaseous form under the reaction conditions selected. Preference is given to amines which decompose to an extent of not more than 2 mol %, particularly preferably not more than 1 mol % and very particularly preferably not more than 0.5 mol %, during the duration of the reaction under the reaction conditions. Particularly suitable amines here are amines, in particular diamines, based on aliphatic or cycloaliphatic hydrocarbons having from 2 to 18 carbon atoms. Examples are 1,6-diaminohexane, 1,5-diaminopentane, 1,3-bis(aminomethyl)-cyclohexane, 1-amino-3,3,5-trimethyl-5-aminomethylcyclohexane (IPDA) and 4,4-diaminodicyclohexylmethane. Preference is given to using 1,6-diaminohexane (HDA).

Aromatic amines which can be brought into the gas phase without significant decomposition can likewise be used for the process of the invention. Examples of preferred aromatic amines are toluenediamine (TDA), as 2,4- or 2,6-isomer or as a mixture thereof, for example as a from 80:20 to 65:35 (mol/mol) mixture, diaminobenzene, 2,6-xylidine, naphthalenediamine (NDA) and 2,4'- or 4,4'-methylenedi (phenylamine) (MDA) or isomer mixtures thereof. Preference is given to 2,4- and/or 2,6-TDA or 2,4'- and/or 4,4'-MDA.

To prepare monoisocyanates, it is likewise possible to use aliphatic, cycloaliphatic or aromatic amines, usually monoamines. A particularly preferred aromatic monoamine is aniline.

In the gas-phase phosgenation, it should be ensured that the compounds occurring during the course of the reaction, i.e. starting materials (amine and phosgene), intermediates (in particular the monocarbamoyl and dicarbamoyl chlorides formed as intermediates), end products (isocyanates) and also any inert compounds introduced, remain in the gas phase under the reaction conditions. Should these or other components deposit from the gas phase onto, for example, the reactor wall or other components of the apparatus, the heat transfer of, or the flow through the components concerned can be altered in an undesirable way by these deposits. This applies, in particular, to amine hydrochlorides formed from free amino groups and hydrogen chloride. The resulting amine hydrochlorides precipitate easily and can be vaporized or decomposed again only with difficulty.

Apart from the use of a tube reactor, it is also possible to use essentially cuboidal reaction spaces, for example plate reactors. Any other desired cross section of the reactor is also possible.

To avoid the formation of by-products, phosgene is preferably employed in excess. To introduce only the proportion of amine necessary for the reaction, it is possible to mix the amine with an inert gas. Inert media which can be added are those which are present in gaseous form in the reaction space and do not react with the compounds occurring during the course of the reaction. Inert media which can be used are, for example, nitrogen, noble gases such as helium or argon, aromatics such as chlorobenzene, o-dichlorobenzene, trichlorobenzene, toluene, xylene, chloronaphthalene, decahydronaphthalene, carbon dioxide or carbon monoxide. Preference is given to using nitrogen and/or chlorobenzene as inert medium.

As an alternative, it is also possible to mix the inert medium into the phosgene, for example to avoid an excessive excess of phosgene.

In general, the inert medium is added in such an amount that the ratio of the gas volume of inert medium to amine or to phosgene is from <0.0001 to 30, preferably from <0.01 to 15 and particularly preferably from <0.1 to 5.

To reduce or avoid the formation of undesirable by-products and also prevent decomposition of the isocyanate formed, the reaction mixture is cooled immediately after the reaction. A quench is preferably used for cooling the reaction mixture. Here, a liquid quenching medium is preferably added. Vaporization of the quenching medium absorbs heat and leads to rapid cooling of the reaction mixture.

The quench can be followed by further cooling devices. Thus, for example, further quenches can be provided. It is also possible to provide indirect cooling in a heat exchanger after the direct cooling in the quench.

To avoid accumulation of nonvolatile residues in the vaporizer in which the amine is vaporized and superheated, a gaseous amine and a purge stream comprising nonvolatile residues are preferably taken off from the vaporizer. In this way, nonvolatile residues can be discharged. The nonvolatile residues can be formed in the vaporizer by decomposition and oligomerization of the amine or have been introduced into the vaporizer. The purge stream enables the nonvolatile residues to be taken off from the vaporizer and thus discharged from the process. To discharge the nonvolatile residues but recover amine which has been carried out at the same time, the purge stream is preferably recirculated to a column for isolating the amine located upstream of the vaporizer. In the column, the amine is preferably separated from other substances by distillation. In this way, amine which has been purified sufficiently for the gas-phase phosgenation can be made available.

The column to which the purge stream is recirculated is, for example, part of a plant for preparing the amine used for preparing the isocyanate.

To vaporize the amine and superheat it to the required reaction temperature of from 200 to 400° C., a salt melt, a fuel gas or steam is preferably used as heating medium which flows through the tubes. When steam is used, this is compressed to a pressure at which the temperature of the steam is above the desired temperature for the superheated amine. Apart from the use of saturated steam, it is also possible to use superheated steam as heating medium. Owing to the small tube diameters required to obtain the necessary specific heat transfer area, heating of the vaporizer by means of a gas is also possible. Apart from superheated steam, it is also possible to use, for example, offgases from a combustion.

Apart from the use of offgases from a combustion, a salt melt or steam, it is also possible to achieve heating by catalytic combustion of a fuel in the tubes. In this case, a fuel is introduced into the tubes of the vaporizer and burnt in the tubes, for example by addition of oxygen, for example in the form of air or oxygen-enriched air. The heat evolved in the combustion is then passed to the amine through the tube walls, as a result of which the amine is vaporized and superheated. To allow catalytic combustion of the fuel, it is possible, for example, to provide the interior walls of the tubes with a catalytically active coating. As catalytically active coating, it is possible to use any desired catalytically active coating known to those skilled in the art. As catalyst, it is usual to use a noble metal, in particular a noble metal of the platinum group, for example platinum or palladium. The metal used as catalyst can then, for example, be deposited on the interior wall of the tube by means of a suitable coating process, for example a vapor deposition process such as chemical vapor deposition (CVD) or physical vapor deposition (PVD). As an alternative, it is also possible to add the catalytically active metal to, for example, a ceramic with which the surfaces of the tubes are coated. However, the catalytically active metal is preferably applied directly to the interior wall of the tubes.

Apart from coating the interior walls with a catalytically active substance, it is also possible, as an alternative, to place the catalyst in the form of, for example, a bed in the tubes. In this case, the catalyst is preferably present as fine granules or as powder.

When the vaporization and superheating of the amine is effected by means of a fuel gas, preferably by catalytic combustion in the tubes, natural gas is preferably used as fuel gas.

When the vaporization of the amine is effected using steam, it may be necessary to install a superheater downstream of the vaporizer in order to bring the amine to the required reaction temperature. This is the case particularly when the temperature of the steam is not high enough to superheat the amine to the reaction temperature. The superheater located downstream of the vaporizer is then heated by means of a heating medium other than steam, for example a fuel gas or a salt melt. The superheater preferably has the same structure as the vaporizer, with the number of tubes and the length of the tubes of vaporizer and superheater being able to be different. As an alternative, it is also possible to use an electrically heated superheater.

As an alternative, it is also possible to construct the vaporizer in two parts, using firstly tubes through which steam flows and, directly after the tubes through which steam flows, tubes in which either a fuel gas is burnt or through which a salt melt flows in order to superheat the amine stream vaporized in the region of the tubes through which steam flows in the subsequent vaporizer part comprising the tubes through which a salt melt flows or the tubes in which a catalytic combustion is carried out.

Heating of the phosgene to the required reaction temperature is likewise effected indirectly by use of a heating medium, for example steam, a salt melt, or by combustion of a fuel or by use of offgases from a combustion as heating medium or else by use of electric heating.

To avoid deposits on the outer wall of the vaporizer for the amine, preference is also given to the outer wall of the vaporizer not having any edges. In particular, preference is given to the outer wall of the vaporizer having a circular or oval cross section. The diameter of the outer wall of the vaporizer can be any desired diameter. The size depends on the amount of amine used and the resulting cross-sectional area through which the amine flows. To avoid the formation of deposits on the outer wall, in particular as a result of a cold outer wall surface, it is also possible to configure the outer wall of the vaporizer as a double wall through which a heating medium can likewise flow. The heating medium here is preferably the same as the heating medium which flows through the tubes of the vaporizer.

EXAMPLES

Comparative Example

A capillary having an inner diameter of 4 mm and a length of 1 m (specific heat transfer area 1000 $m^2/m^3$) has been immersed into a stirred thermal bath of Diphyl with a temperature of 350° C. In the capillary 100 g/h of an isomer mixture of 80% 2,4-TDA and 20% 2,6-TDA with an inlet temperature of 130° C. has been evaporated at a pressure of 3 bar absolute.

After an operating time of 18.3 hours the system had to be shut down due to blockage of the capillary.

Example

A total of 47 capillaries having in outer diameter of 3.17 mm are guided coaxially with a length of 400 mm through a jacket tube. The capillaries are uniformly distributed over the cross section of the jacket tube and hot air at a temperature of about 600° C. is passed through the capillaries. Approximately 2 kg/h of an isomer mixture of 80% 2,4-TDA and 20% 2,6-TDA having an inlet temperature of 120° C. are charged into the jacket space at a pressure of about 4 bar absolute, are vaporized within the jacket space and overheated to an outlet temperature of 430° C. The specific heat transfer area is 950 $m^2/m^3$.

Despite the elevated boiling temperature due to the elevated pressure as well as the additional overheating to 430° C. in difference to the comparative example, TDA could be evaporated in the system for a period of more than 80 hours without any blockage occurring.

The invention claimed is:

1. A process for preparing isocyanates by reacting the corresponding amines with phosgene in the gas phase, in the presence or absence of an inert medium, which comprises the following steps:
    (a) vaporization of the amine in a vaporizer,
    (b) superheating of the amine,
    (c) mixing of the gaseous amine with the phosgene and introduction into a reaction zone,
    (d) reaction of amine and phosgene to give isocyanate in the reaction zone, with a reaction mixture comprising isocyanate and hydrogen chloride being formed,
    (e) cooling of the reaction mixture comprising isocyanate and hydrogen chloride,
    wherein the vaporizer comprises a vessel in which tubes through which a heating medium flows are comprised, where number and diameter of the tubes are designed so that the tubes have a specific heat transfer area based on the volume through which the amine flows of at least 300 $m^2/m^3$.

2. The process according to claim 1, wherein the tubes are arranged parallel to the flow direction of the amine in the vessel.

3. The process according to claim 1, wherein the tubes have a smooth surface.

4. The process according to claim 1, wherein the tubes have a circular cross section.

5. The process according to claim 1, wherein the tubes have an external diameter of not more than 10 mm.

6. The process according to claim 1, wherein the tubes have a length in the range from 0.1 to 5 m.

7. The process according to claim 1, wherein the amine is vaporized and superheated to the reaction temperature and is optionally preheated in the vaporizer.

8. The process according to claim 1, wherein a purge stream comprising gaseous amine and nonvolatile residues is taken off from the vaporizer.

9. The process according to claim 8, wherein at least part of the purge stream is recirculated to a column for isolating the amine located upstream of the vaporizer.

10. The process according to claim 1, wherein the heating medium flowing through the tubes is a salt melt, a fuel gas or steam.

11. The process according to claim 1, wherein heating is effected by catalytic combustion of a fuel in the tubes.

12. The process according to claim 11, wherein the tubes are provided on their interior walls with a catalytically active coating.

* * * * *